(12) United States Patent
Aloni et al.

(10) Patent No.: US 12,239,409 B2
(45) Date of Patent: Mar. 4, 2025

(54) FLUORESCENCE IMAGING CAMERA ASSEMBLY FOR OPEN SURGERY

(71) Applicant: Visionsense Ltd., Petah Tikva (IL)

(72) Inventors: Doron Aloni, Ganey Tikva (IL); Nadav Horesh, Ramat Raziel (IL); Udi Ronen, Kfar Saba (IL)

(73) Assignee: Visionsense Ltd., Petah Tikva (IL)

( * ) Notice: Subject to any disclaimer, the term of this patent is extended or adjusted under 35 U.S.C. 154(b) by 87 days.

(21) Appl. No.: 18/109,425

(22) Filed: Feb. 14, 2023

(65) Prior Publication Data

US 2023/0270330 A1 Aug. 31, 2023

Related U.S. Application Data

(60) Provisional application No. 63/314,602, filed on Feb. 28, 2022.

(51) Int. Cl.
| | |
|---|---|
| *H04N 23/16* | (2023.01) |
| *A61B 5/00* | (2006.01) |
| *H04N 23/11* | (2023.01) |
| *H04N 23/56* | (2023.01) |
| *H04N 23/62* | (2023.01) |
| *H04N 23/667* | (2023.01) |

(52) U.S. Cl.
CPC .......... *A61B 5/0035* (2013.01); *A61B 5/0071* (2013.01); *H04N 23/11* (2023.01); *H04N 23/16* (2023.01); *H04N 23/56* (2023.01); *H04N 23/62* (2023.01); *H04N 23/667* (2023.01); *A61B 2505/05* (2013.01)

(58) Field of Classification Search
CPC . A61B 5/0035; A61B 5/0071; A61B 2505/05; H04N 23/667; H04N 23/56; H04N 23/16; H04N 23/11; H04N 23/62
See application file for complete search history.

(56) References Cited

U.S. PATENT DOCUMENTS

| | | |
|---|---|---|
| 5,546,234 A | 8/1996 | Yamanouchi |
| 7,280,283 B1 | 10/2007 | Kasai |

(Continued)

FOREIGN PATENT DOCUMENTS

WO WO-2019191497 A1 * 10/2019 ............. A61B 1/043

*Primary Examiner* — Thai Q Tran
*Assistant Examiner* — Jose M Mesa
(74) *Attorney, Agent, or Firm* — Carter, DeLuca & Farrell LLP

(57) ABSTRACT

An imaging system includes a visible light source configured to output visible light and a near infrared laser light source configured to output an excitation laser light. The system also includes a camera assembly having: a housing with an opening configured to receive a combined light, which includes visible light and infrared fluorescence light. The combined light entering the housing along a combined light path, the combined light may include visible light and infrared fluorescence light; an aperture mechanism having an adjustable opening disposed along the combined light path; a beamsplitter configured to split the combined light into the visible light along a visible light path and the infrared fluorescence light along an infrared light path; a visible light sensor configured to receive the visible light and to generate visible light image data; and an infrared sensor configured to receive the infrared fluorescence light and to generate infrared fluorescence image data.

14 Claims, 5 Drawing Sheets

(56) References Cited

U.S. PATENT DOCUMENTS

| | | |
|---|---|---|
| 7,453,568 B2 | 11/2008 | Kawamata et al. |
| 7,530,947 B2 | 5/2009 | Yokomise et al. |
| 7,738,180 B2 | 6/2010 | Igarashi |
| 7,843,655 B2 | 11/2010 | Machida |
| 7,876,942 B2 | 1/2011 | Gilboa |
| 7,885,011 B1 | 2/2011 | Wang et al. |
| 7,919,761 B2 | 4/2011 | Ishihara |
| 7,976,461 B2 | 7/2011 | Ertas et al. |
| 8,049,184 B2 | 11/2011 | Ishihara |
| 8,054,184 B2 | 11/2011 | Cline et al. |
| 8,118,730 B2 | 2/2012 | Farr et al. |
| 8,128,558 B2 | 3/2012 | Amling et al. |
| 8,167,794 B2 | 5/2012 | Matsumoto et al. |
| 8,169,470 B2 | 5/2012 | Ishihara et al. |
| 8,229,548 B2 | 7/2012 | Frangioni |
| 8,237,783 B2 | 8/2012 | Yamazaki |
| 8,285,015 B2 | 10/2012 | Demos |
| 8,295,693 B2 | 10/2012 | McDowall |
| 8,345,090 B2 | 1/2013 | Watanabe et al. |
| 8,350,229 B2 | 1/2013 | Watanabe |
| 8,406,860 B2 | 3/2013 | Dvorsky et al. |
| 8,421,034 B2 | 4/2013 | Ono |
| 8,437,629 B2 | 5/2013 | McDowall |
| 8,459,853 B2 | 6/2013 | Hanano |
| 8,472,749 B2 | 6/2013 | Watanabe et al. |
| 8,473,035 B2 | 6/2013 | Frangioni |
| 8,481,972 B2 | 7/2013 | Watanabe |
| 8,489,179 B2 | 7/2013 | Ishihara |
| 8,489,180 B2 | 7/2013 | Morishita et al. |
| 8,493,564 B2 | 7/2013 | Brukilacchio et al. |
| 8,537,210 B2 | 9/2013 | Omori et al. |
| 8,545,399 B2 | 10/2013 | Takei et al. |
| 8,564,652 B2 | 10/2013 | Akiyama et al. |
| 8,570,369 B2 | 10/2013 | Morita |
| 8,654,185 B2 | 2/2014 | Ono |
| 8,682,096 B2 | 3/2014 | Watanabe et al. |
| 8,693,802 B2 | 4/2014 | Watanabe et al. |
| 8,706,184 B2 | 4/2014 | Mohr et al. |
| 8,718,397 B2 | 5/2014 | Watanabe et al. |
| 8,721,532 B2 | 5/2014 | Takei et al. |
| 8,723,936 B2 | 5/2014 | Amling et al. |
| 8,723,937 B2 | 5/2014 | Sasaki |
| 8,767,057 B2 | 7/2014 | Morita |
| 8,767,058 B2 | 7/2014 | Yoshino et al. |
| 8,773,756 B2 | 7/2014 | Tesar et al. |
| 8,831,374 B2 | 9/2014 | Watanabe et al. |
| 8,854,445 B2 | 10/2014 | Yamazaki |
| 8,933,964 B2 | 1/2015 | Yamada |
| 8,965,488 B2 | 2/2015 | Dvorsky et al. |
| 8,967,811 B2 | 3/2015 | Jaffe et al. |
| 8,967,846 B2 | 3/2015 | Jaffe et al. |
| 9,050,012 B2 | 6/2015 | Matsumoto |
| 9,106,848 B2 | 8/2015 | Kamo |
| 9,173,554 B2 | 11/2015 | Fengler et al. |
| 9,182,347 B2 | 11/2015 | Ishihara |
| 9,207,179 B2 | 12/2015 | Ishihara |
| 9,295,392 B2 | 3/2016 | Douplik et al. |
| 9,332,897 B2 | 5/2016 | Watanabe |
| 9,357,902 B2 | 6/2016 | Amling et al. |
| 9,392,942 B2 | 7/2016 | Shida et al. |
| 9,407,838 B2 | 8/2016 | Butte et al. |
| 9,459,415 B2 | 10/2016 | Feingold et al. |
| 9,498,109 B2 | 11/2016 | Ishihara |
| 9,503,692 B2 | 11/2016 | Morita et al. |
| 9,513,219 B2 | 12/2016 | Ishihara |
| 9,516,235 B2 | 12/2016 | Shida |
| 9,516,282 B2 | 12/2016 | Yoshino et al. |
| 9,518,924 B2 | 12/2016 | Kubo et al. |
| 9,519,967 B2 | 12/2016 | Shida et al. |
| 9,521,947 B2 | 12/2016 | Morishita |
| 9,532,719 B2 | 1/2017 | Shida |
| 9,610,021 B2 | 4/2017 | Dvorsky et al. |
| 9,642,532 B2 | 5/2017 | Fengler et al. |
| 9,801,531 B2 | 10/2017 | Morita et al. |
| 9,804,339 B2 | 10/2017 | Fukuoka |
| 9,839,359 B2 | 12/2017 | Kubo et al. |
| 9,872,610 B2 | 1/2018 | Higuchi |
| 9,877,654 B2 | 1/2018 | Tesar |
| 9,901,253 B2 | 2/2018 | Ishihara |
| 9,906,739 B2 | 2/2018 | Sugano et al. |
| 9,936,887 B2 | 4/2018 | Dvorsky et al. |
| 9,949,645 B2 | 4/2018 | Shida et al. |
| 9,986,890 B2 | 6/2018 | Miyai |
| 10,034,600 B2 | 7/2018 | Igarashi |
| 10,038,883 B2 | 7/2018 | Takenaga et al. |
| 10,048,206 B2 | 8/2018 | Hirawake et al. |
| 10,145,796 B2 | 12/2018 | Kuster et al. |
| 10,219,701 B2 | 3/2019 | Ishihara |
| 10,223,779 B2 | 3/2019 | Sato et al. |
| 10,264,236 B2 | 4/2019 | Kiniwa et al. |
| 10,278,585 B2 | 5/2019 | Ferguson, Jr. et al. |
| 10,341,588 B2 | 7/2019 | Richardson et al. |
| 10,345,571 B2 | 7/2019 | Hopkins et al. |
| 10,350,024 B2 | 7/2019 | Kube et al. |
| 10,359,618 B2 | 7/2019 | Williamson et al. |
| 10,362,930 B2 | 7/2019 | Sasaki |
| 10,376,136 B2 | 8/2019 | Kato et al. |
| 10,413,619 B2 | 9/2019 | Ikehara |
| 10,455,201 B2 | 10/2019 | Kouno et al. |
| 10,537,236 B2 | 1/2020 | Bennett et al. |
| 10,564,103 B2 | 2/2020 | Tian et al. |
| 10,568,492 B2 | 2/2020 | Okazaki et al. |
| 10,568,495 B2 | 2/2020 | Yamada et al. |
| 10,575,719 B2 | 3/2020 | Zeien |
| 10,582,832 B2 | 3/2020 | Lawrence et al. |
| 10,602,917 B2 | 3/2020 | King |
| 10,602,918 B2 | 3/2020 | King et al. |
| 10,606,062 B2 | 3/2020 | Duckett, III et al. |
| 10,631,721 B2 | 4/2020 | Kubo |
| 10,650,924 B2 | 5/2020 | Kashima et al. |
| 10,660,505 B2 | 5/2020 | Irion et al. |
| 10,690,904 B2 | 6/2020 | Otterstrom et al. |
| 10,694,151 B2 | 6/2020 | Westwick et al. |
| 10,694,152 B2 | 6/2020 | Westwick et al. |
| 10,708,478 B2 | 7/2020 | Steiner |
| 10,722,106 B2 | 7/2020 | Shiraki et al. |
| 10,750,938 B2 | 8/2020 | Themelis |
| 10,799,087 B2 | 10/2020 | Miyai |
| 10,806,332 B2 | 10/2020 | Duckett, III |
| 10,820,790 B2 | 11/2020 | Nagae |
| 10,823,947 B2 | 11/2020 | Kuster et al. |
| 10,831,020 B2 | 11/2020 | Rehe |
| 10,835,138 B2 | 11/2020 | Dvorsky et al. |
| 10,867,410 B2 | 12/2020 | Yokouchi |
| 10,869,645 B2 | 12/2020 | Fengler et al. |
| 10,904,494 B2 | 1/2021 | Kouno et al. |
| 10,921,252 B2 | 2/2021 | Kaneko |
| 11,025,867 B2 | 6/2021 | Westwick et al. |
| 11,032,481 B2 | 6/2021 | Blanquart |
| 11,221,296 B2 | 1/2022 | Ikenaga et al. |
| 2002/0035310 A1 | 3/2002 | Akui et al. |
| 2007/0083098 A1 | 4/2007 | Stern et al. |
| 2014/0005555 A1 | 1/2014 | Tesar |
| 2015/0157187 A1 | 6/2015 | Cerveri et al. |
| 2019/0000308 A1 | 1/2019 | Duckett, III et al. |
| 2019/0216301 A1 | 7/2019 | Okazaki et al. |
| 2019/0265490 A1 | 8/2019 | Duckett, III |
| 2019/0298157 A1 | 10/2019 | Kuriyama |
| 2020/0163538 A1 | 5/2020 | Takahashi et al. |
| 2020/0205646 A1 | 7/2020 | Tanahashi et al. |
| 2020/0359976 A1 | 11/2020 | Nekovar et al. |
| 2021/0030263 A1 | 2/2021 | Kikuchi et al. |
| 2021/0267443 A1 | 9/2021 | Baumann et al. |

\* cited by examiner

FLUORESCENCE IMAGING CAMERA ASSEMBLY FOR OPEN SURGERY

CROSS-REFERENCE TO RELATED APPLICATIONS

This application claims the benefit of and priority to U.S. Provisional Patent Application No. 63/314,602 filed Feb. 28, 2022. The entire disclosure of the foregoing application is incorporated by referenced herein.

BACKGROUND

Medical imaging is increasingly employing specialized optical imaging techniques, such as fluorescence (i.e., autofluorescence and photodynamic), narrow band imaging and other techniques, for improved visualization and for the detection and diagnosis of diseases. Imaging systems that provide specialized imaging modes also operate in a conventional color, or white light mode.

In conventional white light imaging, light in the visible spectral range is used to illuminate the tissue surface under observation. Light reflected by the tissue passes through a suitable lens system and is incident on an image sensor of a camera unit or an endoscope. The electrical signals from the image sensor are processed into a full color video image which can be displayed on a video monitor or stored in a memory.

In fluorescence-based imaging, fluorescence excitation light excites fluorophores in the tissue, which emit fluorescence light at an emission wavelength, which is typically greater than the excitation wavelength. Fluorescence light from the tissue passes through a suitable lens system and is incident on the image sensor. The electrical signals from the image sensor are processed into a fluorescence video image which can be displayed on a video monitor, either separately or combined with the color video image.

The fluorescence excitation and emission wavelengths depend upon the type of fluorophores being excited. In the case of exogenously applied fluorophores, the band of excitation wavelengths may be located anywhere in the range from the ultraviolet (UV) to the near infra-red (NIR) and the emission wavelength band anywhere from the visible to the NIR. For fluorophores endogenous to tissue, the band of excitation and emission wavelengths are more limited (excitation from the UV to the green part of the visible spectrum, emission from the blue/green light to the NIR). Fluorescence imaging may be used to identify blood vessels, cancer cells, and other tissue types during open surgery.

SUMMARY

According to one embodiment of the present disclosure, a camera assembly is disclosed. The camera assembly includes a housing having an opening configured to receive a combined light entering the housing along a combined light path. The combined light includes visible light and infrared fluorescence light. The camera assembly also includes an aperture mechanism having an adjustable opening disposed along the combined light path. The camera assembly further includes a visible light sensor configured to receive the visible light and to generate visible light image data, and an infrared sensor configured to receive the infrared fluorescence light and to generate infrared fluorescence image data.

Implementations of the above embodiment may include one or more of the following features. According to one aspect of the above embodiment, the aperture mechanism is adjustable at least between a first configuration in which the adjustable opening has a first size and a second configuration in which the adjustable opening has a second size that is smaller than the first size. In the first configuration, the aperture mechanism is configured to increase an amount of near infrared fluorescence light transmitted to the infrared sensor. In the second configuration, the aperture mechanism is configured to increase a depth of field of an image captured by the visible light sensor. The camera assembly may also include a user interface device configured to adjust the aperture mechanism at least between the first configuration and the second configuration. The camera assembly may further include a controller configured to adjust the aperture mechanism at least between the first configuration and the second configuration. The controller may be further configured to operate the camera assembly in an observation mode during which the aperture mechanism is in the first configuration and a navigation mode during which the aperture mechanism is in the second configuration. The camera assembly may additionally include a beamsplitter configured to split the combined light into the visible light along a visible light path and the infrared fluorescence light along an infrared light path, and a notch filter configured to remove excitation laser light from the combined light and a focus group may include at least one lens. The focus group may be disposed between the aperture mechanism and the beamsplitter and movable along the combined light path. The camera assembly may also include a hot mirror disposed along the visible light path between the beamsplitter and the visible light sensor. The hot mirror is configured to transmit the visible light and to reflect the infrared fluorescence light. The camera assembly may also include a bandpass filter disposed along the infrared light path and between the beamsplitter and the infrared sensor. The bandpass filter is configured to transmit only the infrared fluorescence light to the infrared sensor.

According to another embodiment of the present disclosure, an imaging system is disclosed. The imaging system includes a visible light source configured to output visible light and a near infrared laser light source configured to output an excitation laser light. The system also includes a camera assembly having a housing with an opening configured to receive a combined light, which enters the housing along a combined light path. The combined light includes visible light and infrared fluorescence light. The camera assembly also includes an aperture mechanism having an adjustable opening disposed along the combined light path. The camera assembly further includes a visible light sensor configured to receive the visible light and to generate visible light image data and an infrared sensor configured to receive the infrared fluorescence light and to generate infrared fluorescence image data.

Implementations of the above embodiment may include one or more of the following features. According to one aspect of the above embodiment, the aperture mechanism is adjustable at least between a first configuration in which the adjustable opening has a first size and a second configuration in which the adjustable opening has a second size, smaller than the first size. In the first configuration, the aperture mechanism is configured to increase an amount of near infrared fluorescence light transmitted to the infrared sensor. In the second configuration, the aperture mechanism is configured to increase a depth of field of an image captured by the visible light sensor. The imaging system may also include a user interface device configured to adjust the aperture mechanism at least between the first configuration and the second configuration. The imaging system may further include a controller configured to adjust the aperture mechanism at least between the first configuration and the second configuration. The controller is also further configured to operate camera assembly and the near infrared laser light source in an observation mode during which the aperture mechanism is in the first configuration and the near infrared laser light source is activated and a navigation mode during which the aperture mechanism is in the second configuration and the near infrared laser light source is deactivated. The imaging system may also include a motion sensor configured to measure movement of the camera assembly. The controller may be further configured to switch between the observation mode and the navigation mode based on the movement of the camera assembly.

The camera assembly may further include a beamsplitter configured to split the combined light into the visible light along a visible light path and the infrared fluorescence light along an infrared light path and a notch filter configured to remove excitation laser light from the combined light. The camera assembly may also include a focus group having at least one lens. The focus group is disposed between the aperture mechanism and the beamsplitter and is movable along the combined light path. The camera assembly may further include a hot mirror disposed along the visible light path between the beamsplitter and the visible light sensor. The hot mirror is configured to transmit the visible light and to reflect the infrared fluorescence light. The camera assembly may further include a bandpass filter disposed along the infrared light path and between the beamsplitter and the infrared sensor. The bandpass filter is configured to transmit only the infrared fluorescence light to the infrared sensor.

The imaging system may further include an optical cable coupled to the visible light source and the near infrared laser light source. The camera assembly may further include a front lens group disposed within the housing and coupled to the optical cable, the front lens group configured to transmit the visible light and the excitation laser light onto an open surgery operating site.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1:
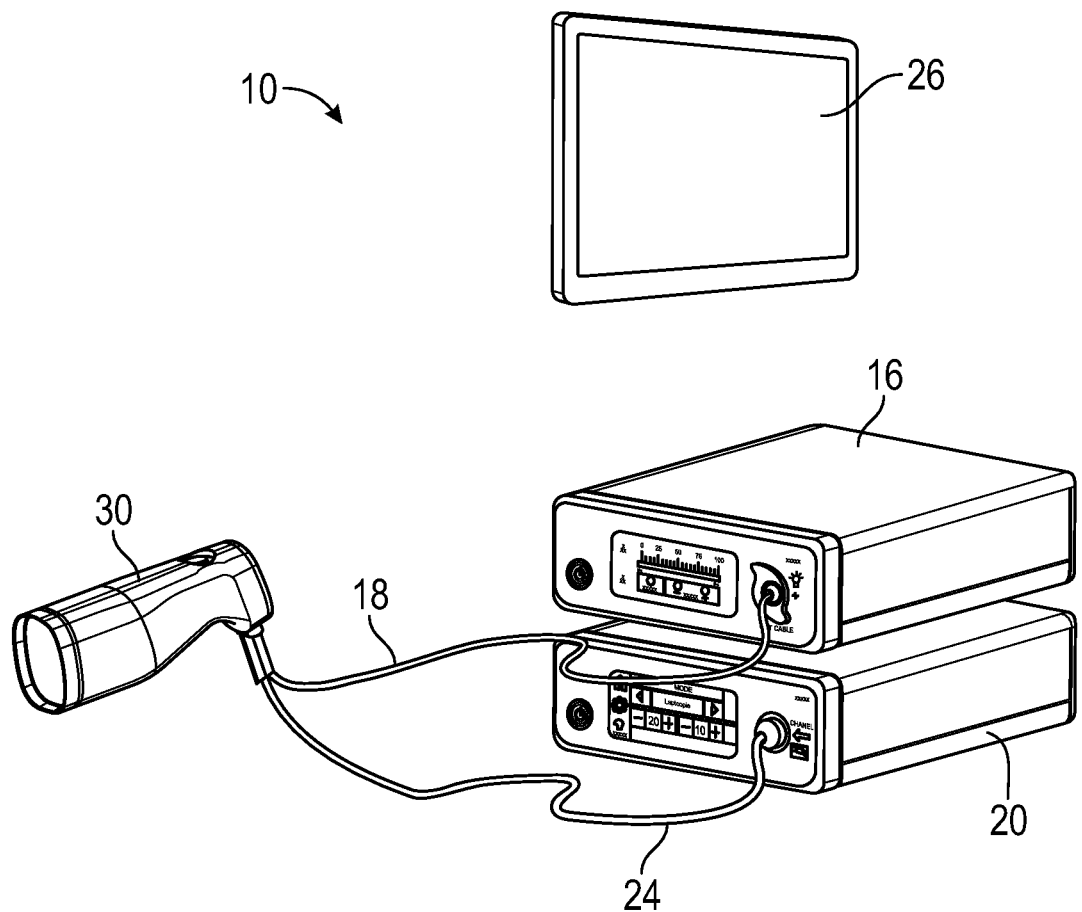
FIG. 1 is a perspective view of an imaging system according to an embodiment the present disclosure.

Embodiments of the presently disclosed system are described in detail with reference to the drawings, in which like reference numerals designate identical or corresponding elements in each of the several views. In the following description, well-known functions or constructions are not described in detail to avoid obscuring the present disclosure in unnecessary detail. Those skilled in the art will understand that the present disclosure may be adapted for use with any imaging system. As used herein the term "distal" refers to that portion of the instrument, or component thereof, farther from the user, while the term "proximal" refers to that portion of the instrument, or component thereof, closer to the user.

With reference to FIG. 1, an imaging system 10 is configured for combined NIR fluorescence and white light imaging during open surgery. With intraoperative usage of fluorophores from a fluorescent dye, such as indocyanine green (ICG), the imaging system 10 enables real-time visual assessment of blood vessels, lymph nodes, lymphatic flow, biliary ducts, and other tissues during surgical procedures. The imaging system 10 provides an adjunctive method for evaluation of tissue perfusion and related tissue-transfer circulation during surgery. The imaging system 10 may utilize NIR excitation laser light having a wavelength of from about 780 nm to about 812 nm and observation range from about 825 nm to about 850 nm. Fluorescence may be provided by a fluorescent dye having matching excitation and emission ranges. The fluorescence light may be detected by an infrared (IR) channel of a camera assembly to produce an IR image. Other channels of the camera assembly may be used to capture white light images of the same scene. Two images, the white light image and the IR image, may be blended and/or combined to produce a composite image.

Figure 2:
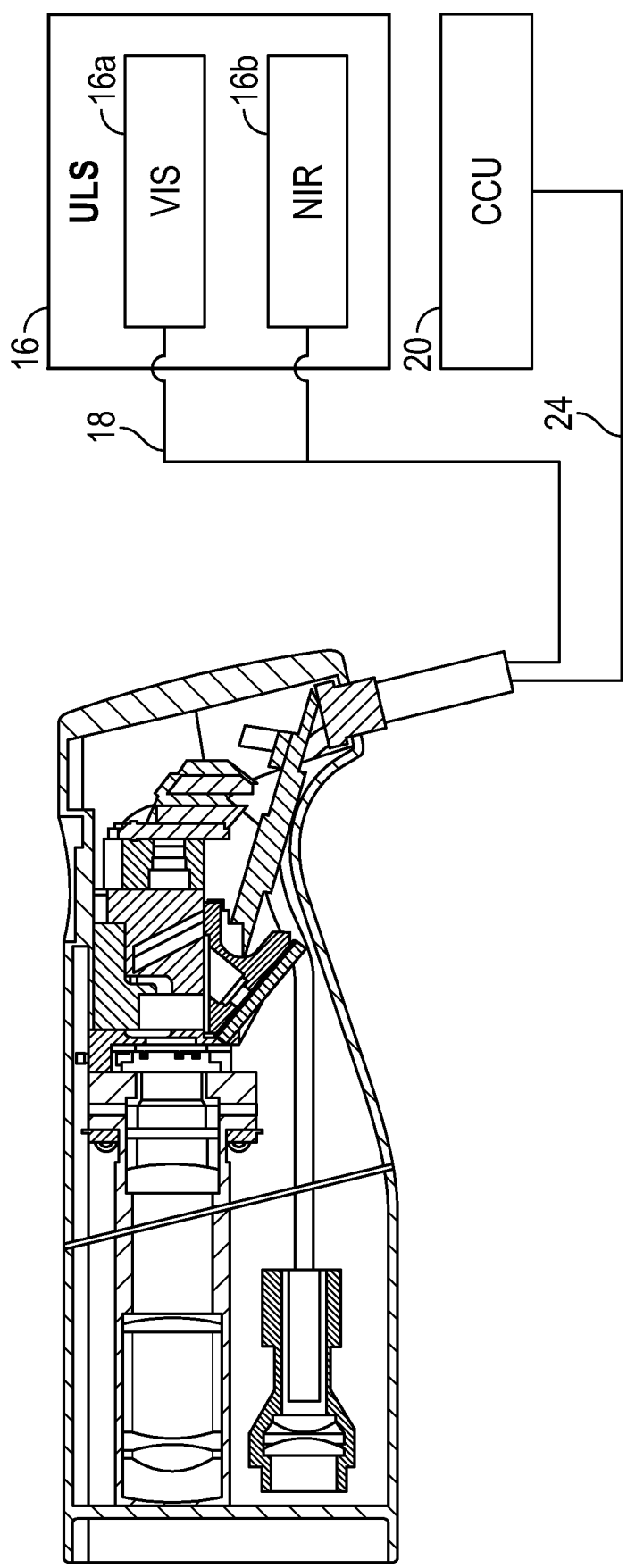
FIG. 2 is a schematic diagram of the imaging system according to an embodiment the present disclosure.

With reference to FIGS. 1 and 2, the imaging system 10 includes a camera assembly 30 having optical components, such as lenses, mirrors, prisms, imaging sensors, and the like, which are described in more detail below with respect to FIGS. 3-5. The camera assembly 30 is coupled to a unified light source (ULS) 16 via an optical cable 18. The ULS 16 may include a white or visible light source 16a and an NIR light source 16b. The visible light source 16a may include one or more light emitting diodes or any other suitable light sources configured to output light in a wavelength range from about 380 nm to about 700 nm. The NIR light source 16b may include a laser diode or any other suitable laser light source having a wavelength from about 780 nm to about 812 nm. In particular, the NIR light source 16b may be a class 1 laser source as defined by U.S. FDA classification and denotes a laser light that is safe to be viewed by a naked eye under all reasonably anticipated conditions, obviating the need for safety eyewear by the patient and/or operating room staff. The use of a class 1 laser provides for a safe operating environment, i.e., without risk of eye injury, without relying on protective measures, such as safety eyewear, which simplifies the operating room procedures.

The light beams from the visible light source 16a and the NIR light source 16b may be collimated or otherwise combined at the ULS 16 using a beamsplitter for transmission along the optical cable 18. In embodiments, the visible light source 16a and the NIR light source 16b may be separate, rather than be enclosed in the ULS 16 and their output combined prior to transmission through the optical cable.

The optical cable 18 may include one or more optical fibers for transmitting the white and NIR light, which illuminates the tissue under observation by the camera assembly 30, which in turn, collects the reflected white and NIR light. The camera assembly 30 is coupled to a camera control unit 20 via a transmission cable 24. The camera control unit 20 is configured to receive the image data signals, process the raw image data from the camera assembly 30, and generate blended white light and NIR images for recording and/or real-time display. The camera control unit 20 also processes the image data signals and outputs the same to a display 26, through any suitable a video output port, such as a DISPLAYPORT™, HDMI®, etc., that can transmit processed images at any desired resolution, display rates, and/or bandwidth.

Figure 3:
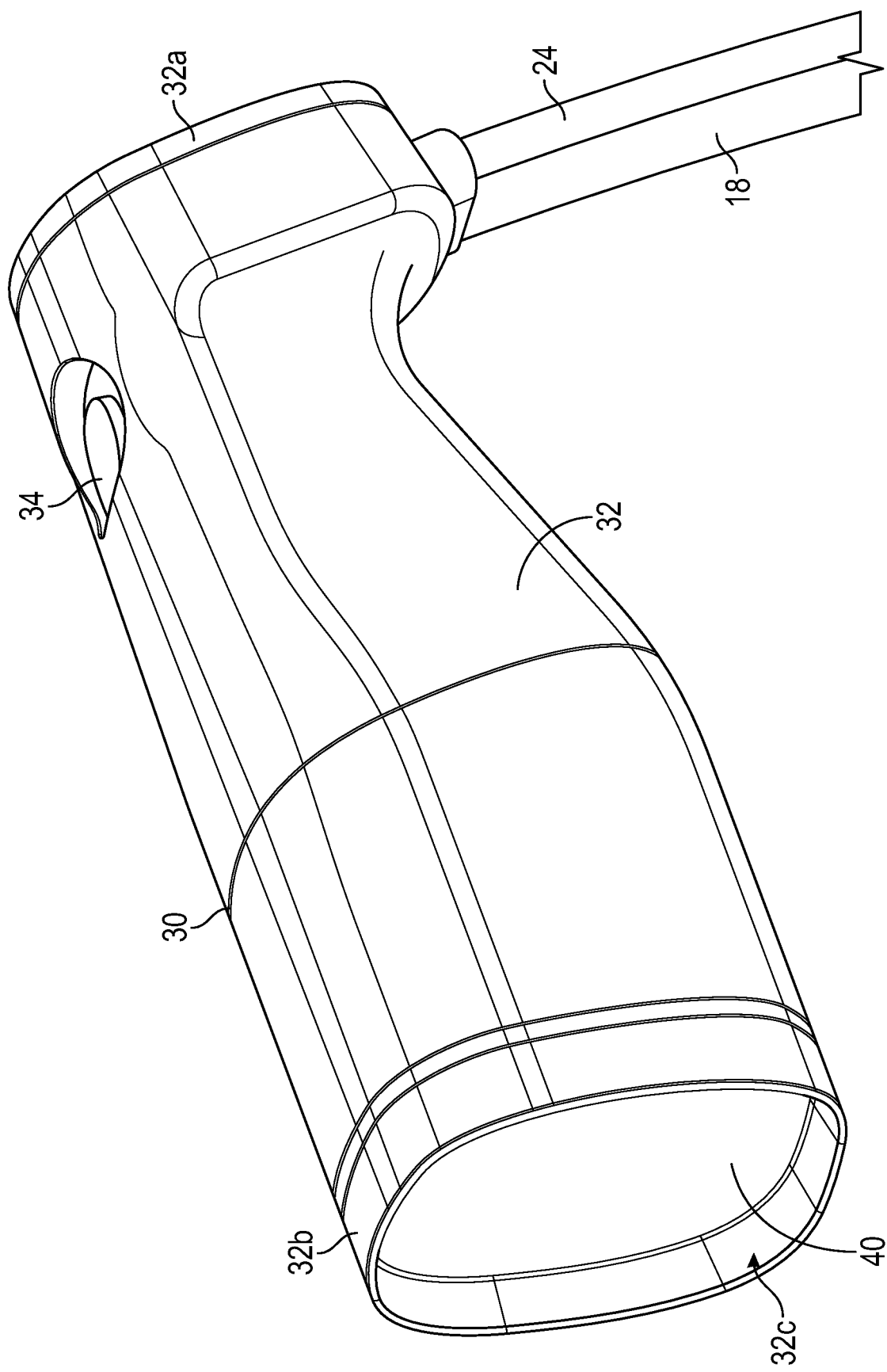
FIG. 3 is a perspective view of a camera assembly according to an embodiment the present disclosure.
Figure 4:
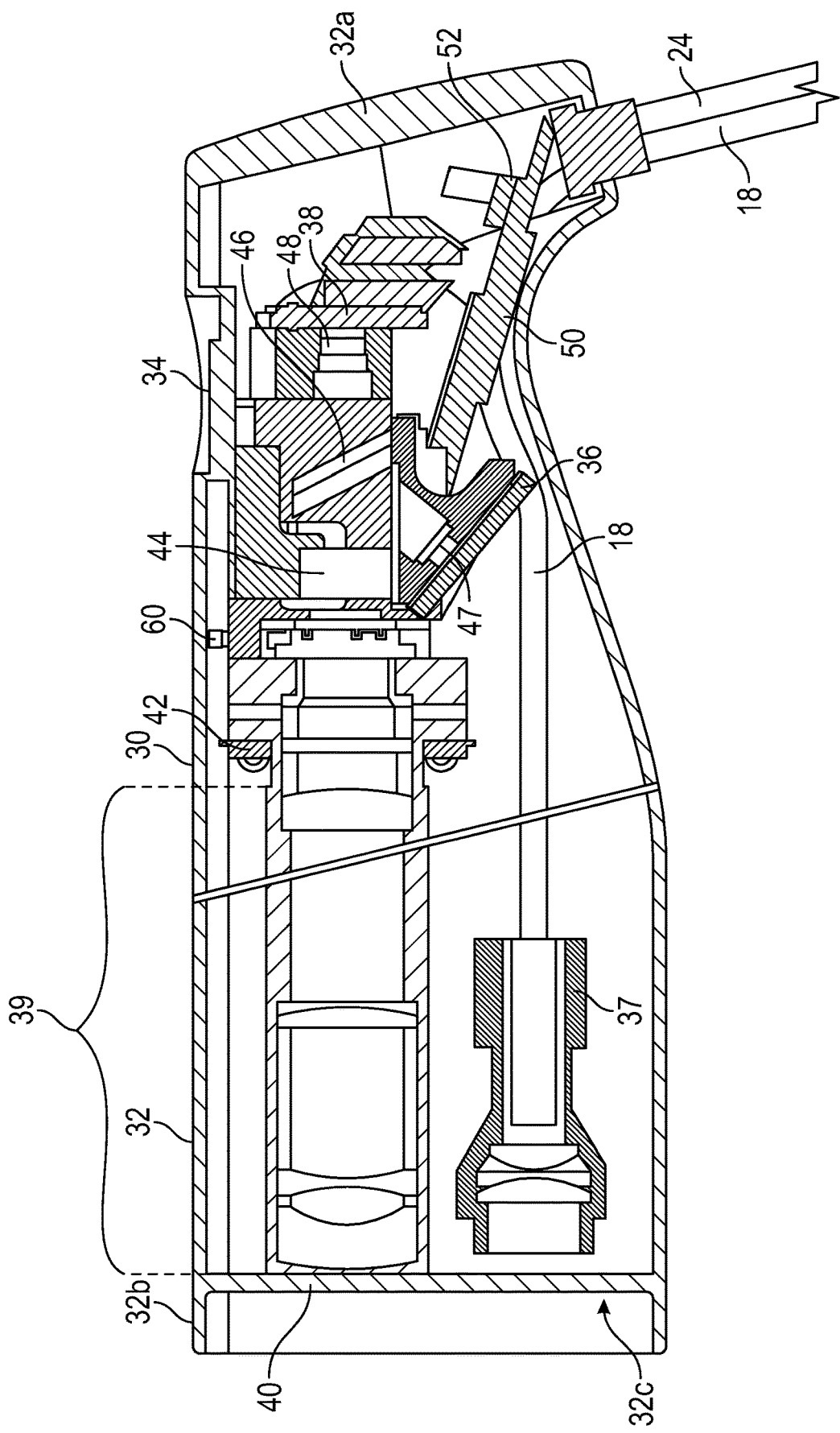
FIG. 4 is a cross-sectional, longitudinal view of the camera assembly of FIG. 3, according to an embodiment the present disclosure.
Figure 5:
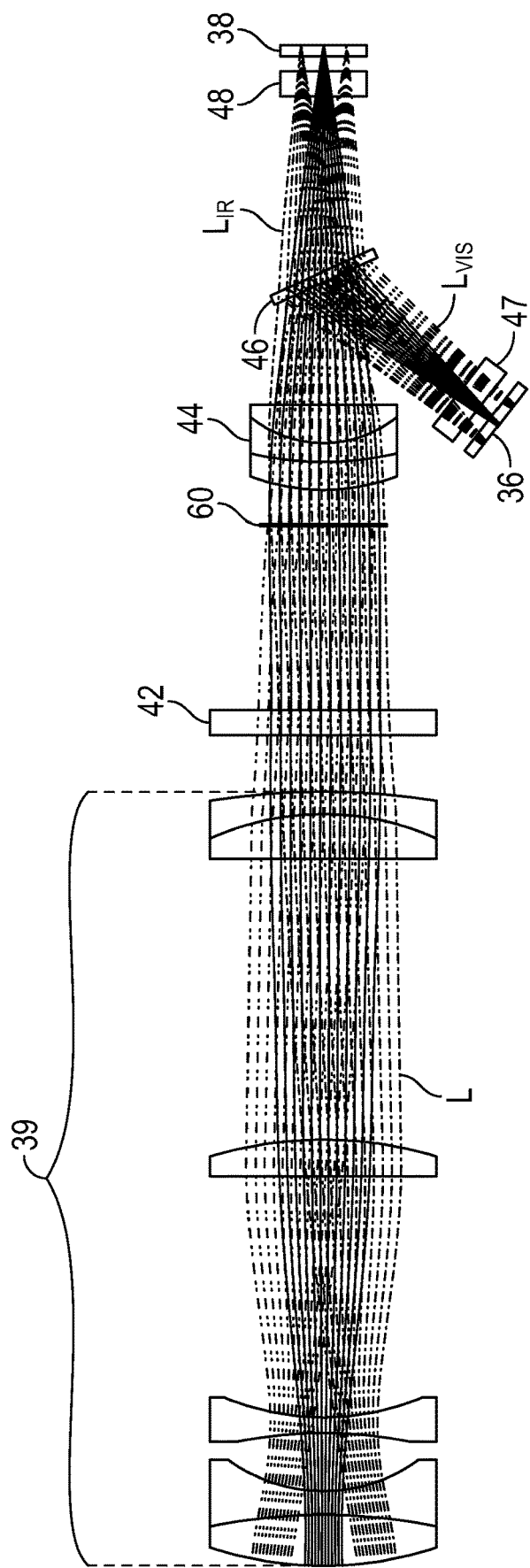
FIG. 5 is a schematic optical diagram of the camera assembly of FIG. 3, according to an embodiment the present disclosure.

With reference to FIGS. 3-5, the camera assembly 30 includes a housing 32 having a proximal end portion 32a and a distal end portion 32b with an opening 32c. The camera assembly 30 may also include a user interface device 34 having one or more inputs (e.g., buttons, touchscreen, etc.) for controlling the camera assembly 30, such as zoom, brightness, etc.

The camera assembly 30 includes a novel optical design and is configured to separate fluorescence wavelengths from undesired components of the light spectrum to specific sensors. In particular, the camera assembly 30 includes a white (e.g., visible) light (VIS) sensor 36 and an IR sensor 38 and is configured to separate and transmit white light to the VIS sensor 36 and fluorescence IR light to the IR sensor 38. The VIS sensor 36 and the IR sensor 38 may be complementary metal oxide semiconductor (CMOS) image sensors having any desired resolution, which in embodiments may be 4K, UHD, etc. In embodiments, a single sensor may be used to perform the functionality of the VIS sensor 36 and the IR sensor.

The camera assembly 30 includes a window 40 disposed at the opening 32c and an illumination lens group 37 that is coupled to the optical cable 18. The illumination lens group 37 is disposed within the housing 32 and is configured to transmit the visible light and the NIR laser light through the window 40 onto an operating site. Thus, optical and imaging elements responsible for illuminating and receiving light are all housed in a single camera assembly 30. Integrating all of the components in the camera assembly 30 allows for easy maneuverability of the camera assembly 30 during open surgical procedures unlike conventional open surgery imaging systems that utilize separate cameras and illumination sources. As used herein, the term "operating site" refers to an open surgical site that may be exposed to ambient light, unlike endoscopic or laparoscopic applications, which are confined to surgical procedures within a closed body cavity.

The combined light, which includes the reflected visible light, reflected NIR laser light, as well as fluorescence IR light, is picked up by the camera assembly 30 and is transmitted along a light path L through the window 40 to a front lens group 39. The combined light is then transmitted through a notch filter 42 that is configured to selectively reject a portion of the combined light. In particular, the notch filter 42 is configured to reject the laser wavelength of the NIR light source 16b, e.g., excitation laser. In embodiments, the notch filter 42 may be configured to reject excitation laser light having a wavelength from about 780 nm to about 812 nm. The notch filter 42 is also configured to passthrough the NIR fluorescence light, which is at a higher wavelength than the excitation laser light, i.e., from about 825 nm to about 850 nm, and visible light which is lower than the excitation laser light, i.e., from about 380 nm to about 700 nm.

The camera assembly 30 also includes a focus group 44 having one or more lenses. The focus group 44 is configured to focus the light on the VIS sensor 36 and the IR sensor 38. This is accomplished by moving the focus group 44 longitudinally along the light path L using any suitable drive mechanism (e.g., piezoelectric actuators). The notch filter 42 may be coupled to the focus group 44 such that the notch filter 42 is also movable along with the focus group 44.

The focus group 44 is coupled to a controller 50 configured to control the focus group 44. In embodiments, the focus group 44 may also be controlled by the camera control unit 20. The controller 50 may be any suitable processor operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be configured to perform operations, calculations, and/or set of instructions described in the disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be any logic processor (e.g., control circuit) adapted to execute algorithms, calculations, and/or set of instructions described herein.

The camera assembly 30 further includes a beamsplitter 46, which may be a cold mirror or any other specialized dielectric mirror that acts as a dichroic filter configured to reflect most or all of the visible light along a VIS light path $L_{VIS}$ while efficiently transmitting IR fluorescence light along IR light path $L_{IR}$. In particular, the beamsplitter 46 is configured to reflect visible light having a wavelength from about 380 nm to about 700 nm and to transmit IR fluorescence light having a wavelength from about 825 nm to about 850 nm. The beamsplitter 46 may be disposed at any incidence angle, which may be from about 10° to about 80° relative to the light path L. The beamsplitter 46 may include a plurality of dielectric coatings disposed in a multi-layer configuration.

The IR light passing through the beamsplitter 46 is then transmitted through a bandpass filter 48 to further eliminate any of the visible light spectrum that may have passed through the beamsplitter 46. The bandpass filter 48 is an optical filter that is configured to selectively transmit a portion of the spectrum, in this case, fluorescence IR light having a wavelength from about 825 nm to about 850 nm, while rejecting all other wavelengths, i.e., visible light and IR laser light. The IR light passes through the bandpass filter 48 and is received by the IR sensor 38, which then outputs image data corresponding to received IR light.

Regarding the visible light that is reflected by the beamsplitter 46, the visible light is transmitted along the VIS light path $L_{VIS}$ at the desired incidence angle that is transverse to the light path L and the IR light path $L_{IR}$. The visible light passes through a hot mirror 47, which is a specialized dielectric mirror, which also acts as a dichroic filter or beamsplitter, that reflects most or all of the IR fluorescence light having a wavelength from about 825 nm to about 850 nm. The hot mirror 47 also efficiently transmits visible light having a wavelength from about 380 nm to about 700 nm along the VIS light path $L_{VIS}$ toward the VIS sensor 36. The hot mirror 47 is disposed substantially perpendicularly to the VIS light path $L_{VIS}$, such that IR light is reflected in a reverse direction along the VIS light path $L_{VIS}$ toward the beamsplitter 46. As used herein, the term "substantially perpendicular" denotes a relative configuration and is +/−5° from true perpendicular of 90°.

The system 10 may be operated in a variety of observational modes during which the visible light source 16a and/or NIR light source 16b are selectively activated. The camera assembly 30 includes an aperture mechanism 60, which may be an iris diaphragm having an adjustable opening centrally disposed relative to the light path L. The aperture mechanism 60 is disposed between the notch filter 42 and the focus group 44. The aperture mechanism 60 is also coupled to the controller 50 and may be adjusted manually by the user through the user interface device 34 or automatically by the controller 50 using any suitable control algorithm, which may be based on one or more measured light properties, state of the camera assembly 30, and/or selected mode. In embodiments, the aperture mechanism 60 may also be controlled by the camera control unit 20.

During use, the NIR light is applied to observe fluorescent tissue, e.g., blood vessels, tumors etc. In order for the fluorescence light to be detectable by the IR sensor 38, the fluorescence light needs to have sufficient intensity. This may be achieved by increasing power of the NIR light source 16b, which in turn would result in a higher powered NIR laser, thus requiring eye protection to be worn by the patient and the operating room staff. Since the excitation laser light using by the imaging system 10 is only a class 1 laser, the resulting fluorescence light is also of lower intensity, thus, the opening of the aperture mechanism 60 is increased to provide for sufficient fluorescence light to be detected by the IR sensor 38. The present disclosure provides for a novel approach utilizing the aperture mechanism 60 to provide for sufficient fluorescent signal for the IR sensor 38 while simultaneously controlling a depth of field. A larger depth of field is used during movement of the camera assembly 30 since this allows maintain the focus of the image.

The aperture mechanism 60 may be adjusted to any desired F stop, e.g., from about 2.8 to about 16. The size of the opening of the aperture mechanism 60 is directly related to the amount of light hitting the IR sensor 38 and inversely related to the depth of field. Thus, the larger opening allows for more fluorescence light hitting the IR sensor 38 while reducing the depth of field. Conversely, the smaller opening reduces the amount of fluorescence light hitting the IR sensor 38 while enlarging the depth of field. The opening of the aperture mechanism 60 is adjusted based on selected operational mode of the camera assembly 30, i.e., whether the camera assembly 30 is used to detect fluorescence light while the camera assembly 30 is stationary or whether the camera assembly 30 is being moved to image a different portion of the operating site.

The camera assembly 30 may be operated in a first mode, i.e., observational mode, while the camera assembly 30 is stationary. During this mode the NIR light source 16b is active and the aperture mechanism 60 is adjusted to a first configuration, i.e., large aperture. This allows for the IR sensor 38 to receive sufficient fluorescence light to enable fluorescent observation of the operating site. In other words, the larger opening enlarges the amount of light that is incident of the IR sensor 38 without increasing the power of the NIR laser output by the NIR light source 16b. Furthermore, the depth of field is reduced accordingly due to the large aperture. Thus, in the first mode, the fluorescence detection, i.e., functionality of the IR sensor 38, is prioritized over depth of field, i.e., functionality of the VIS sensor 36. However, since the camera assembly 30 is stationary, the reduced depth of field is sufficient for focusing on the operating site using the focus group 44, and in particular on a specific region of interest. As used herein the region of interest includes a specific feature of the operating site, which may be determined using a computer vision algorithm derived from machine learning techniques, such as a deep neural network trained to recognize and identify type, position, orientation, operational state of a surgical instrument, an end effectors, a fiducial markers, an anatomical feature, etc.

The camera assembly 30 may also be operated in a second mode, i.e., navigational mode, while the camera assembly 30 is moved to image a different portion of the operating site. During this mode the NIR light source 16b may be active but the aperture mechanism 60 is adjusted to a second configuration, i.e., small aperture. This provides for a larger depth of field, extending the focus further. The VIS sensor 36 is responsible for providing an in-focus image during movement of the camera assembly 30. Thus, in the second mode, the depth of field, i.e., functionality of the VIS sensor 36, is prioritized over fluorescence detection i.e., functionality of the IR sensor 38. Furthermore, the depth of field is enlarged accordingly due to the small aperture. Since the camera assembly 30 is moving, the enlarged depth of field allows for focusing on the operating site using the focus group 44. The focus group 44 is also adjusted automatically by the controller 50 to keep the operating site in focus during movement of the camera assembly 30.

In embodiments, the NIR light source 16b may be activated during the first, i.e., observational, mode and deactivated during the second, i.e., navigational mode. Switching between modes may be done manually by the user, which would activate or deactivate the NIR light source 16b as well as adjust the size of the opening of the aperture mechanism 60. In embodiments, switching between the two modes may be done automatically by detecting movement of the camera assembly 30.

The camera assembly 30 may also include one or more motion sensors 52, which may be an accelerometer, a gyroscope, an inertial measurement unit, or any other suitable sensor configured to measure movement, tilting, and/or pivoting of the camera assembly 30. The motion sensor 52 is coupled to the controller 50 and is configured to provide motion data to the controller 50, which then determines whether the camera assembly 30 is being operated in the first mode or the second mode based on the motion data. The controller 50 may then switch the NIR light source 16b as well as the aperture mechanism 60 based on the identified mode.

The above disclosed optical configuration of the camera assembly 30 separates and filters visible and IR light along divergent paths, allowing for use of two separate sensors (i.e., the VIS sensor 36 and the IR sensor 38). This allows for operating the VIS sensor 36 and the IR sensor 38 at highest possible frame rates for each of the visible and IR light channels, resulting in a smoother video stream while combining visible and IR images. Furthermore, filtering of the light through the notch filter 42, the beamsplitter 46, and the bandpass filter 48 allows for using a highly sensitive IR sensor 38, which normally would not be possible due to higher intensity IR light present in the reflect light. Using higher sensitivity IR sensors 38 is beneficial in identifying critical tissue elements, such as cancer cells.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. A camera assembly comprising:
a housing having an opening configured to receive a combined light, which enters the housing along a combined light path, the combined light including visible light and infrared fluorescence light;
an aperture mechanism having an adjustable opening disposed along the combined light path, wherein the aperture mechanism is adjustable at least between a first configuration in which the adjustable opening has a first size and a second configuration in which the adjustable opening has a second size that is smaller than the first size;
a visible light sensor configured to receive the visible light and to generate visible light image data;
an infrared sensor configured to receive the infrared fluorescence light and to generate infrared fluorescence image data; and
a controller configured to:
adjust the aperture mechanism at least between the first configuration and the second configuration;
operate the camera assembly in an observation mode during which the aperture mechanism is in the first configuration and a navigation mode during which the aperture mechanism is in the second configuration, wherein the controller activates a near infrared light source while the camera assembly is operable in the observation mode and deactivates the near infrared light source while the camera assembly is operable in the navigation mode.

2. The camera assembly according to claim 1, wherein in the first configuration, the aperture mechanism is configured to increase an amount of near infrared fluorescence light transmitted to the infrared sensor.

3. The camera assembly according to claim 1, wherein in the second configuration, the aperture mechanism is configured to increase a depth of field of an image captured by the visible light sensor.

4. The camera assembly according to claim 1, further comprising:
a user interface device configured to adjust the aperture mechanism at least between the first configuration and the second configuration.

5. The camera assembly according to claim 1, further comprising:
a beamsplitter configured to split the combined light into the visible light along a visible light path and the infrared fluorescence light along an infrared light path;
a notch filter configured to remove excitation laser light from the combined light; and
a focus group including at least one lens, the focus group disposed between the aperture mechanism and the beamsplitter and movable along the combined light path.

6. The camera assembly according to claim 5, further comprising:
a hot mirror disposed along the visible light path between the beamsplitter and the visible light sensor, the hot mirror configured to transmit the visible light and to reflect the infrared fluorescence light.

7. The camera assembly according to claim 5, further comprising:
a bandpass filter disposed along the infrared light path and between the beamsplitter and the infrared sensor, the bandpass filter configured to transmit only the infrared fluorescence light to the infrared sensor.

8. An imaging system comprising:
a visible light source configured to output visible light;
a near infrared laser light source configured to output an excitation laser light; and
a camera assembly including:
a housing having an opening configured to receive a combined light, which enters the housing along a combined light path, the combined light including visible light and infrared fluorescence light;
an aperture mechanism having an adjustable opening disposed along the combined light path, wherein the aperture mechanism is adjustable at least between a first configuration in which the adjustable opening has a first size and a second configuration in which the adjustable opening has a second size that is smaller than the first size;
a visible light sensor configured to receive the visible light and to generate visible light image data; and
an infrared sensor configured to receive the infrared fluorescence light and to generate infrared fluorescence image data; and
a controller configured to:
adjust the aperture mechanism at least between the first configuration and the second configuration; and
operate the camera assembly and the near infrared laser light source in an observation mode during which the aperture mechanism is in the first configuration and the near infrared laser light source is activated and a navigation mode during which the aperture mechanism is in the second configuration and the near infrared laser light source is deactivated.

9. The imaging system according to claim 8, wherein in the first configuration, the aperture mechanism is configured to increase an amount of near infrared fluorescence light transmitted to the infrared sensor.

10. The imaging system according to claim 8, wherein in the second configuration, the aperture mechanism is configured to increase a depth of field of an image captured by the visible light sensor.

11. The imaging system according to claim 8, further comprising:
a user interface device configured to adjust the aperture mechanism at least between the first configuration and the second configuration.

12. The imaging system according to claim 8, further comprising a motion sensor configured to measure movement of the camera assembly, wherein the controller is further configured to switch between the observation mode and the navigation mode based on the movement of the camera assembly.

13. The imaging system according to claim 8, an optical cable coupled to the visible light source and the near infrared laser light source, wherein the camera assembly further includes front lens group disposed within the housing and coupled to the optical cable, the front lens group configured to transmit the visible light and the excitation laser light onto an open surgery operating site.

14. The imaging system according to claim 8, wherein the camera assembly further includes:
a beamsplitter configured to split the combined light into the visible light along a visible light path and the infrared fluorescence light along an infrared light path;
a notch filter configured to remove excitation laser light from the combined light;
a focus group including at least one lens, the focus group disposed between the aperture mechanism and the beamsplitter and movable along the combined light path;

a hot mirror disposed along the visible light path between the beamsplitter and the visible light sensor, the hot mirror configured to transmit the visible light and to reflect the infrared fluorescence light; and a bandpass filter disposed along the infrared light path and between the beamsplitter and the infrared sensor, the bandpass filter configured to transmit only the infrared fluorescence light to the infrared sensor.

\* \* \* \* \*